(12) United States Patent
Boulais (10) Patent No.: US 8,052,597 B2
(45) Date of Patent: Nov. 8, 2011

(54) METHOD FOR FORMING AN ENDOSCOPE ARTICULATION JOINT

(75) Inventor: Dennis R Boulais, Danielson, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1081 days.

(21) Appl. No.: 11/215,704

(22) Filed: Aug. 30, 2005

(65) Prior Publication Data
US 2007/0049800 A1    Mar. 1, 2007

(51) Int. Cl.
*A61B 1/00* (2006.01)
(52) U.S. Cl. .................................. 600/141; 600/142
(58) Field of Classification Search .................. 600/125, 600/144, 114, 121, 139–142, 146, 149, 150
See application file for complete search history.

(56) References Cited

U.S. PATENT DOCUMENTS

| | | | |
|---|---|---|---|
| 3,266,059 A * | 8/1966 | Stelle | 623/62 |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,621,618 A | 11/1986 | Omagari et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |

(Continued)

FOREIGN PATENT DOCUMENTS
EP        0 689 851 A1    1/1996
(Continued)

*Primary Examiner* — Matthew J Kasztejna
*Assistant Examiner* — Ryan Henderson
(74) *Attorney, Agent, or Firm* — Finnegan, Henderson, Farabow, Garrett & Dunner, L.L.P.

(57) ABSTRACT

In one aspect, the present invention is an articulation joint for use in a low cost medical device such as an endoscope intended for a single use. In one embodiment, the articulation joint comprises a plurality of interconnected segments. In another embodiment, the articulation joint comprises an elongated tubular body. In another aspect, the present invention provides methods of manufacturing an articulation joint for use in a medical device.

30 Claims, 9 Drawing Sheets

U.S. PATENT DOCUMENTS

| | | | |
|---|---|---|---|
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okabe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi |
| 5,174,293 A | 12/1992 | Hagiwara |
| 5,176,629 A | 1/1993 | Kullas et al. |
| 5,179,935 A * | 1/1993 | Miyagi .................. 600/142 |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |
| 5,325,845 A | 7/1994 | Adair et al. |
| 5,331,551 A | 7/1994 | Tsuruoka et al. |
| 5,342,299 A | 8/1994 | Snoke et al. |
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matumoto |
| 5,436,640 A | 7/1995 | Reeves |
| 5,436,767 A | 7/1995 | Suzuki et al. |
| 5,440,341 A | 8/1995 | Suzuki et al. |

| | | | | | |
|---|---|---|---|---|---|
| 5,464,007 A | 11/1995 | Krauter et al. | 5,876,373 A | 3/1999 | Giba et al. |
| 5,469,840 A | 11/1995 | Tanii et al. | 5,876,427 A | 3/1999 | Chen et al. |
| 5,473,235 A | 12/1995 | Lance et al. | 5,877,819 A | 3/1999 | Branson |
| 5,482,029 A | 1/1996 | Sekiguchi et al. | 5,879,284 A | 3/1999 | Tsujita |
| 5,484,407 A | 1/1996 | Osypka | 5,880,714 A | 3/1999 | Rosenberg et al. |
| 5,485,316 A | 1/1996 | Mori et al. | 5,882,293 A | 3/1999 | Ouchi |
| 5,496,260 A | 3/1996 | Krauter et al. | 5,882,339 A | 3/1999 | Beiser et al. |
| 5,515,449 A | 5/1996 | Tsuruoka et al. | 5,889,670 A | 3/1999 | Schuler et al. |
| 5,518,501 A | 5/1996 | Oneda et al. | 5,889,672 A | 3/1999 | Schuler et al. |
| 5,543,831 A | 8/1996 | Tsuji et al. | 5,892,630 A | 4/1999 | Broome |
| 5,569,158 A | 10/1996 | Suzuki et al. | 5,895,350 A | 4/1999 | Hori |
| 5,569,159 A | 10/1996 | Anderson et al. | 5,897,507 A | 4/1999 | Kortenbach et al. |
| 5,586,262 A | 12/1996 | Komatsu et al. | 5,897,525 A | 4/1999 | Dey et al. |
| 5,589,854 A | 12/1996 | Tsai | 5,907,487 A | 5/1999 | Rosenberg et al. |
| 5,591,202 A | 1/1997 | Slater et al. | 5,923,018 A | 7/1999 | Kameda et al. |
| 5,608,451 A | 3/1997 | Konno et al. | 5,928,136 A | 7/1999 | Barry |
| 5,619,380 A | 4/1997 | Agasawa et al. | 5,929,607 A | 7/1999 | Rosenberg et al. |
| 5,622,528 A | 4/1997 | Hamano et al. | 5,929,846 A | 7/1999 | Rosenberg et al. |
| 5,631,695 A | 5/1997 | Nakamura et al. | 5,929,900 A | 7/1999 | Yamanaka |
| 5,633,203 A | 5/1997 | Adair | 5,929,901 A | 7/1999 | Adair et al. |
| 5,643,203 A | 7/1997 | Beiser et al. | 5,931,833 A | 8/1999 | Silverstein |
| 5,645,075 A | 7/1997 | Palmer et al. | 5,933,809 A | 8/1999 | Hunt et al. |
| 5,647,840 A | 7/1997 | D'Amelio et al. | 5,935,085 A | 8/1999 | Welsh et al. |
| 5,658,238 A | 8/1997 | Suzuki et al. | 5,936,778 A | 8/1999 | Miyano et al. |
| 5,667,477 A | 9/1997 | Segawa | 5,941,817 A | 8/1999 | Crawford |
| 5,674,182 A | 10/1997 | Suzuki et al. | 5,950,168 A | 9/1999 | Simborg et al. |
| 5,674,197 A | 10/1997 | van Muiden et al. | 5,951,462 A | 9/1999 | Yamanaka |
| 5,685,823 A | 11/1997 | Ito et al. | 5,956,416 A | 9/1999 | Tsuruoka et al. |
| 5,685,825 A | 11/1997 | Takase et al. | 5,956,689 A | 9/1999 | Everhart |
| 5,691,853 A | 11/1997 | Miyano | 5,956,690 A | 9/1999 | Haggerson et al. |
| 5,695,450 A | 12/1997 | Yabe et al. | 5,959,613 A | 9/1999 | Rosenberg et al. |
| 5,698,866 A | 12/1997 | Doiron et al. | 5,976,070 A | 11/1999 | Ono et al. |
| 5,702,349 A | 12/1997 | Morizumi | 5,976,074 A | 11/1999 | Moriyama |
| 5,703,724 A | 12/1997 | Miyano | 5,980,454 A | 11/1999 | Broome |
| 5,704,371 A | 1/1998 | Shepard | 5,980,468 A | 11/1999 | Zimmon |
| 5,704,896 A | 1/1998 | Fukunishi et al. | 5,986,693 A | 11/1999 | Adair et al. |
| 5,708,482 A | 1/1998 | Takahashi et al. | 5,991,729 A | 11/1999 | Barry et al. |
| 5,721,566 A | 2/1998 | Rosenberg et al. | 5,991,730 A | 11/1999 | Lubin et al. |
| 5,724,068 A | 3/1998 | Sanchez et al. | 5,999,168 A | 12/1999 | Rosenberg et al. |
| 5,728,045 A | 3/1998 | Komi | 6,002,425 A | 12/1999 | Yamanaka et al. |
| 5,739,811 A | 4/1998 | Rosenberg et al. | 6,007,531 A | 12/1999 | Snoke et al. |
| 5,740,801 A | 4/1998 | Branson | 6,014,630 A | 1/2000 | Jeacock et al. |
| 5,746,696 A | 5/1998 | Kondo | 6,015,088 A | 1/2000 | Parker et al. |
| 5,749,828 A * | 5/1998 | Solomon et al. ............ 600/141 | 6,017,322 A | 1/2000 | Snoke et al. |
| 5,764,809 A | 6/1998 | Nomami et al. | 6,020,875 A | 2/2000 | Moore et al. |
| 5,767,839 A | 6/1998 | Rosenberg | 6,020,876 A | 2/2000 | Rosenberg et al. |
| 5,781,172 A | 7/1998 | Engel et al. | 6,026,363 A | 2/2000 | Shepard |
| 5,788,714 A | 8/1998 | Ouchi | 6,030,360 A | 2/2000 | Biggs |
| 5,789,047 A | 8/1998 | Sasaki et al. | 6,032,120 A | 2/2000 | Rock et al. |
| 5,793,539 A | 8/1998 | Konno et al. | 6,039,728 A | 3/2000 | Berlien et al. |
| 5,805,140 A | 9/1998 | Rosenberg et al. | 6,043,839 A | 3/2000 | Adair et al. |
| 5,810,715 A | 9/1998 | Moriyama | 6,050,718 A | 4/2000 | Schena et al. |
| 5,812,983 A | 9/1998 | Kumagai | 6,057,828 A | 5/2000 | Schena et al. |
| 5,819,736 A | 10/1998 | Avny et al. | 6,059,719 A | 5/2000 | Yamamoto et al. |
| 5,820,591 A | 10/1998 | Thompson et al. | 6,061,004 A | 5/2000 | Rosenberg |
| 5,821,466 A | 10/1998 | Clark et al. | 6,067,077 A | 5/2000 | Martin et al. |
| 5,821,920 A | 10/1998 | Rosenberg et al. | 6,071,248 A | 6/2000 | Zimmon |
| 5,823,948 A | 10/1998 | Ross, Jr. et al. | 6,075,555 A | 6/2000 | Street |
| 5,827,186 A | 10/1998 | Chen et al. | 6,078,308 A | 6/2000 | Rosenberg et al. |
| 5,827,190 A | 10/1998 | Palcic et al. | 6,078,353 A | 6/2000 | Yamanaka et al. |
| 5,828,197 A | 10/1998 | Martin et al. | 6,078,876 A | 6/2000 | Rosenberg et al. |
| 5,828,363 A | 10/1998 | Yaniger et al. | 6,080,104 A | 6/2000 | Ozawa et al. |
| 5,830,124 A | 11/1998 | Suzuki et al. | 6,081,809 A | 6/2000 | Kumagai |
| 5,830,128 A | 11/1998 | Tanaka | 6,083,152 A | 7/2000 | Strong |
| 5,836,869 A | 11/1998 | Kudo et al. | 6,083,170 A | 7/2000 | Ben-Haim |
| 5,837,023 A | 11/1998 | Koike et al. | 6,095,971 A | 8/2000 | Takahashi |
| 5,840,014 A | 11/1998 | Miyano et al. | 6,099,465 A | 8/2000 | Inoue |
| 5,841,126 A | 11/1998 | Fossum et al. | 6,100,874 A | 8/2000 | Schena et al. |
| 5,843,000 A | 12/1998 | Nishioka et al. | 6,104,382 A | 8/2000 | Martin et al. |
| 5,846,183 A | 12/1998 | Chilcoat | 6,120,435 A | 9/2000 | Eino |
| 5,855,560 A | 1/1999 | Idaomi et al. | 6,125,337 A | 9/2000 | Rosenberg et al. |
| 5,857,963 A | 1/1999 | Pelchy et al. | 6,128,006 A | 10/2000 | Rosenberg et al. |
| 5,865,724 A | 2/1999 | Palmer et al. | 6,132,369 A | 10/2000 | Takahashi |
| 5,868,664 A | 2/1999 | Speier et al. | 6,134,056 A | 10/2000 | Nakamuka |
| 5,868,666 A | 2/1999 | Okada et al. | 6,134,506 A | 10/2000 | Rosenberg et al. |
| 5,873,816 A | 2/1999 | Kagawa et al. | 6,135,946 A | 10/2000 | Konen et al. |
| 5,873,866 A | 2/1999 | Kondo et al. | 6,139,508 A | 10/2000 | Simpson et al. |
| 5,876,326 A | 3/1999 | Takamura et al. | 6,141,037 A | 10/2000 | Upton et al. |
| 5,876,331 A | 3/1999 | Wu et al. | 6,142,956 A | 11/2000 | Kortenbach et al. |

| Patent | Type | Date | Inventor |
|---|---|---|---|
| 6,146,355 | A | 11/2000 | Biggs |
| 6,149,607 | A | 11/2000 | Simpson et al. |
| 6,152,877 | A | 11/2000 | Masters |
| 6,154,198 | A | 11/2000 | Rosenberg |
| 6,154,248 | A | 11/2000 | Ozawa et al. |
| 6,155,988 | A | 12/2000 | Peters |
| 6,181,481 | B1 | 1/2001 | Yamamoto et al. |
| 6,184,922 | B1 | 2/2001 | Saito et al. |
| 6,193,714 | B1 | 2/2001 | McGaffigan et al. |
| 6,195,592 | B1 | 2/2001 | Schuler et al. |
| 6,203,493 | B1 | 3/2001 | Ben-Haim |
| 6,206,824 | B1 | 3/2001 | Ohara et al. |
| 6,211,904 | B1 | 4/2001 | Adair |
| 6,216,104 | B1 | 4/2001 | Moshfeghi et al. |
| 6,219,091 | B1 | 4/2001 | Yamanaka et al. |
| 6,221,070 | B1 | 4/2001 | Tu et al. |
| 6,241,668 | B1 | 6/2001 | Herzog |
| 6,260,994 | B1 | 7/2001 | Matsumoto et al. |
| 6,270,453 | B1 | 8/2001 | Sakai |
| 6,272,470 | B1 | 8/2001 | Teshima |
| 6,275,255 | B1 | 8/2001 | Adair et al. |
| 6,283,960 | B1 | 9/2001 | Ashley |
| 6,295,082 | B1 | 9/2001 | Dowdy et al. |
| 6,299,625 | B1 | 10/2001 | Bacher |
| 6,309,347 | B1 | 10/2001 | Takahashi et al. |
| 6,310,642 | B1 | 10/2001 | Adair et al. |
| 6,319,196 | B1 | 11/2001 | Minami |
| 6,319,197 | B1 | 11/2001 | Tsuji et al. |
| 6,334,844 | B1 | 1/2002 | Akiba |
| 6,346,075 | B1 | 2/2002 | Arai et al. |
| 6,366,799 | B1 | 4/2002 | Acker et al. |
| 6,381,029 | B1 | 4/2002 | Tipirneni |
| 6,398,724 | B1 | 6/2002 | May et al. |
| 6,413,207 | B1 | 7/2002 | Minami |
| 6,421,078 | B1 | 7/2002 | Akai et al. |
| 6,425,535 | B1 | 7/2002 | Akiba |
| 6,425,858 | B1 | 7/2002 | Minami |
| 6,436,032 | B1 | 8/2002 | Eto et al. |
| 6,441,845 | B1 | 8/2002 | Matsumoto |
| 6,447,444 | B1 | 9/2002 | Avni et al. |
| 6,449,006 | B1 | 9/2002 | Shipp |
| 6,453,190 | B1 | 9/2002 | Acker et al. |
| 6,454,162 | B1 | 9/2002 | Teller |
| 6,459,447 | B1 | 10/2002 | Okada et al. |
| 6,468,204 | B2 | 10/2002 | Sendai et al. |
| 6,475,141 | B2 | 11/2002 | Abe |
| 6,478,730 | B1 | 11/2002 | Bala et al. |
| 6,482,149 | B1 | 11/2002 | Torii |
| 6,489,987 | B1 | 12/2002 | Higuchi et al. |
| 6,496,827 | B2 | 12/2002 | Kozam et al. |
| 6,498,948 | B1 | 12/2002 | Ozawa et al. |
| 6,503,193 | B1 | 1/2003 | Iwasaki et al. |
| 6,506,196 | B1 * | 1/2003 | Laufer ............ 606/142 |
| 6,520,908 | B2 | 2/2003 | Ikeda et al. |
| 6,524,234 | B2 | 2/2003 | Ouchi |
| 6,530,882 | B1 | 3/2003 | Farkas et al. |
| 6,533,722 | B2 | 3/2003 | Nakashima |
| 6,540,669 | B2 | 4/2003 | Abe et al. |
| 6,544,194 | B1 | 4/2003 | Kortenbach et al. |
| 6,545,703 | B1 | 4/2003 | Takahashi et al. |
| 6,551,239 | B2 | 4/2003 | Renner et al. |
| 6,558,317 | B2 | 5/2003 | Takahashi et al. |
| 6,561,971 | B1 | 5/2003 | Akiba |
| 6,565,507 | B2 | 5/2003 | Kamata et al. |
| 6,574,629 | B1 | 6/2003 | Cooke, Jr. et al. |
| 6,589,162 | B2 | 7/2003 | Nakashima et al. |
| 6,595,913 | B2 | 7/2003 | Takahashi |
| 6,597,390 | B1 | 7/2003 | Higuchi |
| 6,599,239 | B2 | 7/2003 | Hayakawa et al. |
| 6,602,186 | B1 | 8/2003 | Sugimoto et al. |
| 6,605,035 | B2 | 8/2003 | Ando et al. |
| 6,609,135 | B1 | 8/2003 | Omori et al. |
| 6,611,846 | B1 | 8/2003 | Stoodley |
| 6,614,969 | B2 | 9/2003 | Eichelberger et al. |
| 6,616,601 | B2 | 9/2003 | Hayakawa |
| 6,623,424 | B2 | 9/2003 | Hayakawa et al. |
| 6,638,214 | B2 | 10/2003 | Akiba |
| 6,638,215 | B2 | 10/2003 | Kobayashi |
| 6,641,528 | B2 * | 11/2003 | Torii ............ 600/142 |
| 6,651,669 | B1 | 11/2003 | Burnside |
| 6,656,110 | B1 | 12/2003 | Irion et al. |
| 6,656,112 | B2 | 12/2003 | Miyanaga |
| 6,659,940 | B2 | 12/2003 | Adler |
| 6,663,561 | B2 | 12/2003 | Sugimoto et al. |
| 6,669,629 | B2 | 12/2003 | Matsui |
| 6,673,012 | B2 | 1/2004 | Fujii et al. |
| 6,677,984 | B2 | 1/2004 | Kobayashi et al. |
| 6,678,397 | B1 | 1/2004 | Ohmori et al. |
| 6,682,479 | B1 | 1/2004 | Takahashi et al. |
| 6,685,631 | B2 | 2/2004 | Minami |
| 6,686,949 | B2 | 2/2004 | Kobayashi et al. |
| 6,690,409 | B1 | 2/2004 | Takahashi |
| 6,690,963 | B2 | 2/2004 | Ben-Haim et al. |
| 6,692,431 | B2 | 2/2004 | Kazakevich |
| 6,697,101 | B1 | 2/2004 | Takahashi et al. |
| 6,699,181 | B2 | 3/2004 | Wako |
| 6,702,737 | B2 | 3/2004 | Hinto et al. |
| 6,711,426 | B2 | 3/2004 | Benaron et al. |
| 6,715,068 | B1 | 3/2004 | Kazunori |
| 6,716,162 | B2 | 4/2004 | Hakamata |
| 6,728,599 | B2 | 4/2004 | Wang et al. |
| 6,730,018 | B2 | 5/2004 | Takase |
| 6,736,773 | B2 | 5/2004 | Wendlandt et al. |
| 6,743,240 | B2 | 6/2004 | Smith et al. |
| 6,749,559 | B1 | 6/2004 | Krass et al. |
| 6,749,560 | B1 | 6/2004 | Konstorum et al. |
| 6,749,561 | B2 | 6/2004 | Kazakevich |
| 6,753,905 | B1 | 6/2004 | Okada et al. |
| 6,758,806 | B2 * | 7/2004 | Kamrava et al. ............ 600/153 |
| 6,758,807 | B2 | 7/2004 | Minami |
| 6,758,842 | B2 | 7/2004 | Irion et al. |
| 6,778,208 | B2 | 8/2004 | Takeshige et al. |
| 6,780,151 | B2 | 8/2004 | Grabover et al. |
| 6,785,410 | B2 | 8/2004 | Vining et al. |
| 6,785,593 | B2 | 8/2004 | Wang et al. |
| 6,796,938 | B2 | 9/2004 | Sendai |
| 6,796,939 | B1 | 9/2004 | Hirata et al. |
| 6,798,533 | B2 | 9/2004 | Tipirneni |
| 6,800,056 | B2 | 10/2004 | Tartaglia et al. |
| 6,800,057 | B2 | 10/2004 | Tsujita et al. |
| 6,808,491 | B2 | 10/2004 | Kortenbach et al. |
| 6,824,539 | B2 | 11/2004 | Novak |
| 6,824,548 | B2 | 11/2004 | Smith et al. |
| 6,829,003 | B2 | 12/2004 | Takami |
| 6,830,545 | B2 | 12/2004 | Bendall |
| 6,832,990 | B2 | 12/2004 | Kortenbach et al. |
| 6,840,932 | B2 | 1/2005 | Lang et al. |
| 6,842,196 | B1 | 1/2005 | Swift et al. |
| 6,846,286 | B2 | 1/2005 | Suzuki et al. |
| 6,847,933 | B1 | 1/2005 | Hastings |
| 6,849,043 | B2 | 2/2005 | Kondo |
| 6,850,794 | B2 | 2/2005 | Shahidi |
| 6,855,109 | B2 | 2/2005 | Obata et al. |
| 6,858,004 | B1 | 2/2005 | Ozawa et al. |
| 6,858,014 | B2 | 2/2005 | Damarati |
| 6,860,849 | B2 | 3/2005 | Matsushita et al. |
| 6,863,650 | B1 | 3/2005 | Irion |
| 6,863,661 | B2 | 3/2005 | Carrillo et al. |
| 6,868,195 | B2 | 3/2005 | Fujita |
| 6,871,086 | B2 | 3/2005 | Nevo et al. |
| 6,873,352 | B2 | 3/2005 | Mochida et al. |
| 6,876,380 | B2 | 4/2005 | Abe et al. |
| 6,879,339 | B2 | 4/2005 | Ozawa |
| 6,881,188 | B2 | 4/2005 | Furuya et al. |
| 6,882,785 | B2 | 4/2005 | Eichelberger et al. |
| 6,887,195 | B1 | 5/2005 | Pilvisto |
| 6,890,294 | B2 | 5/2005 | Niwa et al. |
| 6,892,090 | B2 | 5/2005 | Verard et al. |
| 6,892,112 | B2 | 5/2005 | Wang et al. |
| 6,895,268 | B1 | 5/2005 | Rahn et al. |
| 6,898,086 | B2 | 5/2005 | Takami et al. |
| 6,899,673 | B2 | 5/2005 | Ogura et al. |
| 6,899,674 | B2 | 5/2005 | Viebach et al. |
| 6,899,705 | B2 | 5/2005 | Niemeyer |
| 6,900,829 | B1 | 5/2005 | Ozawa et al. |
| 6,902,527 | B1 | 6/2005 | Doguchi et al. |
| 6,902,529 | B2 | 6/2005 | Onishi et al. |
| 6,903,761 | B1 | 6/2005 | Abe et al. |

| | | |
|---|---|---|
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0034863 A1 | 2/2003 | Kazakevich |
| 2003/0036748 A1 | 2/2003 | Cooper |
| 2003/0069897 A1 | 4/2003 | Roy et al. |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0075538 A1 | 4/2005 | Banik |
| 2005/0197861 A1 | 9/2005 | Omori et al. |
| 2005/0203341 A1 | 9/2005 | Welker et al. |
| 2005/0228697 A1 | 10/2005 | Funahashi |
| 2005/0272978 A1 * | 12/2005 | Brunnen et al. .............. 600/142 |
| 2005/0273085 A1 * | 12/2005 | Hinman et al. ................ 606/1 |
| 2006/0111615 A1 * | 5/2006 | Danitz et al. ................. 600/141 |

FOREIGN PATENT DOCUMENTS

| | | |
|---|---|---|
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 3372273 B2 | 11/2002 |
| JP | 2003-75113 A | 3/2003 |
| JP | 3482238 B2 | 10/2003 |
| WO | WO 93/13704 A1 | 7/1993 |
| WO | WO 2004/016310 A2 | 2/2004 |
| WO | WO 2005/023082 A2 | 3/2005 |

* cited by examiner

- 400: Method for Manufacturing An Articulation Joint
- 410: Injection molding a plurality of segments. Each segment is a cylinder with an outer wall and a central lumen. The outer wall includes a number of hinges and a plurality of slots therethrough.
- 420: Injection molding a plurality of cable guide elements. Each cable guide element has a passage adapted to be inserted in the slots and into the central lumen of the segments.
- 430: Interconnecting at least two segments and inserting the cable guide elements into the slots.
- 440: Threading one or more cables through the passages on the cable guide elements.
- 450: Tensioning the cables to form the articulation joint.
- 460: END

METHOD FOR FORMING AN ENDOSCOPE ARTICULATION JOINT

FIELD OF THE INVENTION

The present invention relates to medical devices in general and to articulation joints for use in medical devices in particular.

BACKGROUND OF THE INVENTION

It has become well established that there are major health benefits from regular endoscopic examinations of a patient's internal structures such as the alimentary canals and airways, e.g., the esophagus, stomach, lungs, colon, uterus, urethra, kidney, and other organ systems. Endoscopes are also commonly used to perform surgical, therapeutic, diagnostic, or other medical procedures under direct visualization. A conventional imaging endoscope used for such procedures includes an illuminating mechanism such as a fiber optic light guide connected to a proximal source of light, and an imaging means such as an imaging light guide to carry an image to a remote camera, or eye piece, or a miniature video camera within the endoscope itself. In addition, most endoscopes include one or more working channels through which medical devices such as biopsy forceps, snares, fulguration probes and other tools may be passed in order to perform a procedure at a desired location in the patient's body.

Navigation of the endoscope through complex and tortuous paths is critical to the success of the examination with minimum pain, side effects, risk or sedation to the patient. To this end, modern endoscopes include means for deflecting the distal tip of the scope to follow the pathway of the structure under examination, with minimum deflection or friction force upon the surrounding tissue. Control cables similar to bicycle brake cables are carried within the endoscope body in order to connect an articulation joint adjacent to the distal end to a set of control knobs at the proximal endoscope handle. By manipulating the control knobs, the operator is usually able to steer the endoscope during insertion and direct it to a region of interest. Common operator complaints about traditional endoscopes include their limited flexibility, limited column strength, and limited operator control of stiffness along the endoscope length.

Conventional endoscopes are expensive, hand assembled medical devices costing in the range of $25,000 for an endoscope, and much more for the associated operator console. Because of this expense, these conventional endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments that frequently need expensive repair as a result of damage during use or during a disinfection procedure.

Low cost, disposable medical devices designated for a single use have become popular for instruments that are difficult to clean properly. Single-use, disposable devices are packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. One medical device that has not previously been inexpensive enough to be considered truly disposable is the endoscope, such as a colonoscope, bronchoscope, gastroscope, duodenoscope, etc. Such a single-use or disposable endoscope is described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc., and are hereby incorporated by reference.

The articulation joint adjacent to the distal tip of a conventional endoscope is typically made from complicated stamped and formed parts that are brazed together. The brazing operation is expensive and the metal articulation joint segments require special tooling to produce. In addition, adhesives are often used to assemble the articulation joint segments to each other. Therefore, a need exists for a method of producing articulation joints from low cost materials that are easily assembled for use in a low-cost medical device such as a disposable endoscope.

SUMMARY OF THE INVENTION

To address these and other concerns, in one embodiment the present invention is an articulation joint for use in a medical device such as an endoscope. The articulation joint is comprised of a number of low cost, easily mass produced components that allow the distal end of the endoscope to be bent in a desired direction by one or more control cables. In one embodiment, the articulation joint body comprises a plurality of interconnecting segments. Each segment comprises a cylinder with an outer wall and a central lumen. The outer wall includes a number of hinge elements therein and a series of slots therethrough. A plurality of cable guide elements having a passage for control cables are inserted into the slots and two or more cables are threaded through the plurality of cable guide elements and tensioned to form the articulation joint body.

In another embodiment, the articulation joint body is a tubular body comprising a cylinder with an outer wall and a central lumen. The outer wall includes a number of hinge elements therein and a series of slots therethrough. A plurality of annular rings are snap-fitted around the circumference of the tubular body at spaced intervals. Each annular ring has an outer circumference with a first end and a second end and a space therebetween. Also included in each annular ring is at least one pair of inwardly extending cable guide loops adapted to be inserted into the slots in the outer wall of the tubular body. Two or more cables are threaded through the plurality of cable guide loops and tensioned to form the articulation joint body.

In another aspect, the present invention includes a method of manufacturing an articulation joint for use in a medical device; In one embodiment, the method comprises injection molding a plurality of segments having interconnecting structures. Each segment comprises a cylinder with an outer wall and a central lumen. The outer wall includes a number of hinge elements therein and a series of slots therethrough. The method includes injection molding a plurality of cable guide elements that each have a passage element adapted to be inserted through the slots on the outer wall. The method involves interconnecting two or more segments and inserting the cable guide elements into the slots in the outer walls of the segments. One or more cables are then threaded through the guide elements and tensioned to form the articulation joint.

In another embodiment, the method comprises injection molding a tubular body comprising a cylinder with an outer wall and a central lumen. The outer wall includes a number of hinge elements and a series of slots therethrough. A plurality of annular rings are formed, each ring having two or more guide loops sized to be received in the slots in the outer wall.

The annular rings are snap-fitted over the tubular body such that the guide loops are fitted through the slots and at least two cables are threaded through the guide loops and tensioned to form the articulation joint.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Generally described, the present invention provides an articulation joint and a method of making an articulation joint for use in a medical device, such as an endoscope. The present invention provides many advantages over articulation joints used in conventional endoscopy systems. For example, the articulation joints of the present invention are easy to assemble and do not require the use of adhesives or brazing, thereby providing an inexpensive and easily mass-produced joint that allows the distal end of a medical device, such as an endoscope, to be bent in any desired direction by one or more control cables.

The various embodiments of the articulation joint described herein may be used with both conventional reusable endoscopes and low cost, disposable endoscopes, such as those described in U.S. patent application Ser. No. 10/811,781, filed Mar. 29, 2004, and in a U.S. Continuation-in-Part patent application Ser. No. 10/956,007, filed Sep. 30, 2004, that are assigned to Scimed Life Systems, Inc., now Boston Scientific Scimed, Inc., and are hereby incorporated by reference.

Figure 1:
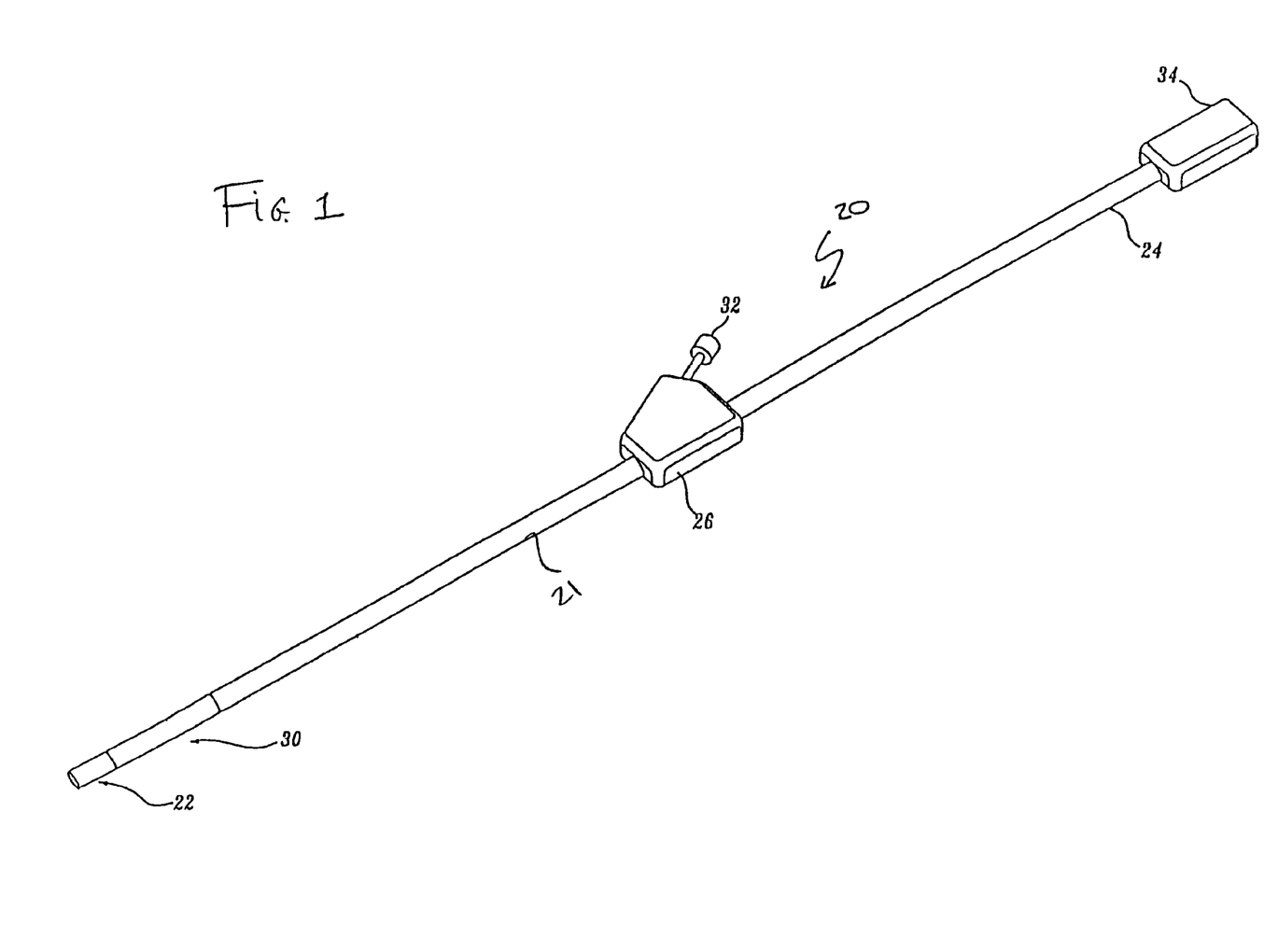
FIG. 1 is a diagram illustrating a representative embodiment of an endoscope having a distal end, a proximal end and an articulation joint adjacent the distal end formed in accordance with an embodiment of the present invention.

FIG. 1 illustrates an exemplary endoscope 20, having an embodiment of an articulation joint 30 formed in accordance with the present invention. The endoscope 20 can be any single-use or reusable, flexible, or partially-flexible elongated probe, such as, for example, a bronchoscope or a colonoscope. In the embodiment shown in FIG. 1, the endoscope 20 includes an elongated shaft 21 with a distal end 22 that is advanced into a patient's body cavity and a proximal end 24 that is removably connected to a control cabinet (not shown) via a connector 34. The endoscope 20 includes the articulation joint 30 proximal to the distal tip 22 to provide sufficient flexibility to the distal section of the shaft 21 such that the distal end 22 can be directed over the required deflection range (180° or more). The endoscope 20 has a set of control cables 40, shown best in FIG. 2, that control the motion of the distal end 22. The distal end of the control cables are attached at or adjacent to the distal end 22 of the shaft, while the proximal ends of the control cables are attached to actuators in a handle (not shown) or in a control unit (not shown).

In the embodiment shown in FIG. 1, the endoscope 20 also includes a breakout box 26 that is positioned approximately midway along the length of the endoscope. The breakout box 26 provides an entrance to a working channel covered by a cap 32. In use, an operator can remove the cap 32 and insert a medical device such as a biopsy forceps, snare, etc., into the working channel of the endoscope to perform a desired procedure within the patient.

Figure 2:
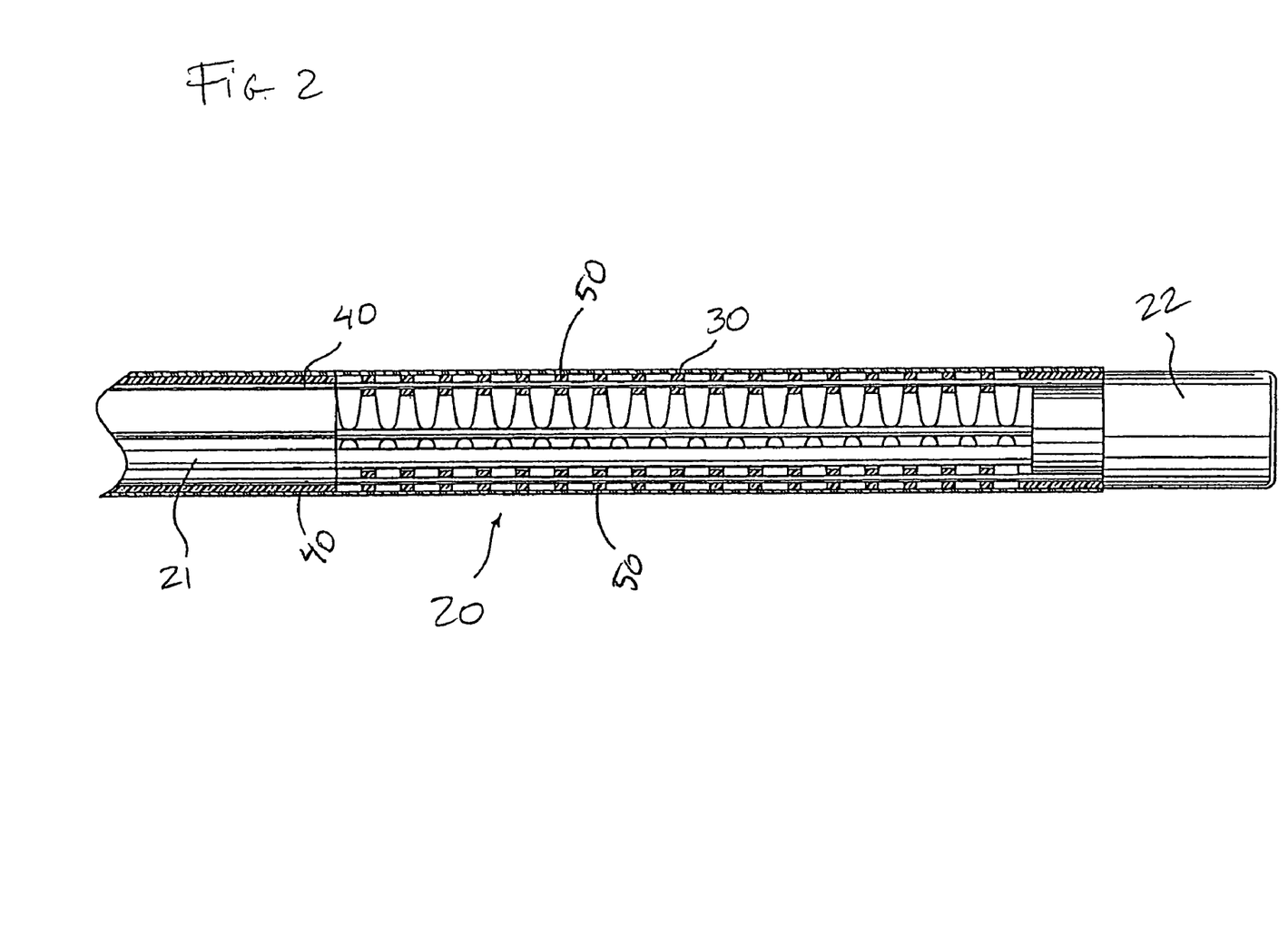
FIG. 2 illustrates an articulation joint positioned adjacent a distal portion of an endoscope shaft in accordance with an embodiment of the present invention.

FIG. 2 is a longitudinal, cross-sectional view of the distal portion of the shaft 21 of the endoscope 20 in accordance with one embodiment of the present invention. The endoscope 20 generally comprises a hollow shaft having one or more lumens formed of plastic materials, such as polyurethane or polyethylene, which terminate at the distal end 22. The shape of the distal end 22 and shaft 21 are usually cylindrical but can be made in other shapes to facilitate passage into a body cavity. The distal end 22 comprises a cap that is secured within a central lumen to the distal end of the articulation joint 30. The distal end of the shaft 21 is secured to the proximal end of the articulation joint 30. In some embodiments, the shaft 21 has a greater torsional stiffness and/or is better able to transmit torque towards the distal end of the endoscope than at the proximal end of the endoscope. The cap at the distal end 22 includes an imaging system with a light illumination port, an image sensor, an opening to a working channel, and a flushing port. Further detail of an exemplary imaging system and its operation can be found in U.S. patent application Ser. Nos. 10/811,781, and 10/956,007, as discussed above.

With continued reference to FIG. 2, a number of control cables 40 extend from the proximal end of the shaft 21 where they connect to actuators in the control cabinet or a manual handle (not shown). The control cables 40 extend through a plurality of cable guide elements 50 positioned along the walls of the articulation joint 30, and terminate either at the distal end of the articulation joint 30 or in the distal end section 22. The proximal portion of the control cables 40 may be routed within the center lumen of the shaft 21, or, as shown in FIG. 2, may be routed through a number of cable guide elements or lumens formed within or along the walls of the shaft 21, as discussed in more detail below.

Figures 3A, 3B, 3C:
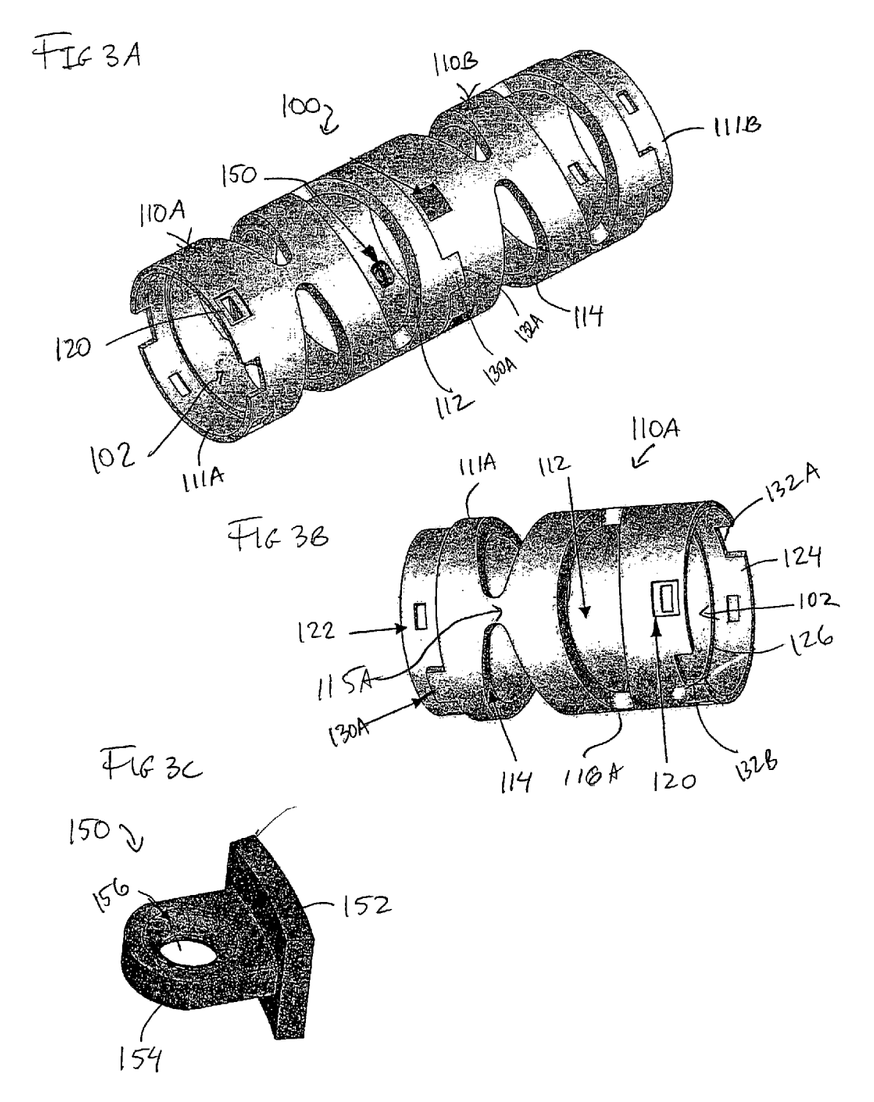
FIG. 3A illustrates a partial view of an articulation joint body comprising a plurality of interconnected segments in accordance with an embodiment of the present invention.
FIG. 3B is a detailed view of a segment of the articulation joint body shown in FIG. 3A.
FIG. 3C is a perspective view of a cable guide element for use in assembling an articulation joint body comprising a plurality of interconnected segments in accordance with an embodiment of the present invention.

In accordance with the various aspects of the invention, the articulation joint 30 has a generally cylindrical configuration with a central lumen. In one embodiment, shown in FIG. 3A, an articulation joint body 100 is formed from a plurality of interconnected segments 110A, 110B that are axially aligned and secured to one another to create an articulation joint. FIG. 3B shows further detail of the segment 110A. The articulation joint segment 110 comprises a cylindrical tube having an outer wall 111A and an open central lumen 102. One or more hinges 112, 114 are formed in the outer wall 111A along the longitudinal axes in order to facilitate bending of the assembled articulation joint body 100. In one embodiment, as shown in FIG. 3A, each segment comprises two pairs of hinge elements 112, 114. Each hinge 112, 114 comprises a pair of opposing V-shaped slits in the outer wall 111A that are separated by a pair of opposing flex points 115A, 155B (hidden in FIG. 3B) and 116A, 166B (hidden in FIG. 3B) in the outer wall 111A. Upon tension of the control cables, each hinge allows the segment and/or the assembled tubular body comprising multiple segments to move back and forth in an amount that is determined by the widest part of the V-shaped slits. In the embodiment of the articulation joint body 100 shown in FIG. 3A, the hinges 112 and 114 are circumferentially arranged in an alternating 90 degree pattern to achieve articulation in two planes, although other arrangements would also be known to one of skill in the art. As will be appreciated, the angles of the V-shaped cuts that form the hinges 112 and 114 may be uniform, or may vary along the length of the articulation joint body 100. Similarly, the distance between adjacent hinges 112 and 114 may be uniform or may vary in order to tailor the bending and torque fidelity characteristics of the articulation joint body 100. The segments 110A, 110B, etc., are preferably made from a molded plastic material and include a central lumen 102 through which the control cables 40 and other elements of the endoscope 20 are passed to allow electrical, irrigation and aspiration connections to extend into the distal end 22. Suitable materials for forming the articulation joint segments 110A, 110B include polyurethane, polyethylene, polypropylene or other biocompatible polymers.

The articulation joint body 100 may be formed from any number of interconnecting segments 110A, 110B, etc., in order to provide an articulation joint having any total bend angle required. For example, in one embodiment of the articulation joint body 100, each segment includes the hinge 112 and 114, each having a closing angle of 30 degrees. In accordance with this embodiment, six segments 110A, 110B, 110C, 110D, 110E, and 110F (not shown), having a corresponding total of six hinges 112 and 114 for each axis disposed along the length of the articulation joint are required to provide a 360 degree range of movement.

FIGS. 3A and 3B additionally illustrate a representative set of interconnecting structures capable of interlocking the segments 110A and 110B to form a portion of the articulation joint body 100. As shown in FIG. 3B, the segment 110A comprises an outer wall 111A having a first end 122 and a second end 124. The first end 122 of the segment 110A includes an outwardly extending rim having an outer diameter selected such that the rim is able to be received in a corresponding counter-bored detail of an adjacent segment. As further shown in FIGS. 3A and 3B, one end of the segment includes a set of tangs 130 and a set of notches 132 on the other end. The tangs 130 from one segment are received in the notches 132 of an adjacent segment to prevent the adjacent segments from axially rotating with respect to each other.

In the embodiment of the articulation joint body 100 shown in FIG. 3A, the outer wall 111A of the segment 110A at the proximal-most end of the articulation joint body 100 is adapted to receive the distal end of the shaft 21, and the outer wall 111B of segment 110B at the distal-most end of the articulation joint body 100 is adapted to receive the distal end 22 of the endoscope 20.

With reference now to FIG. 3B, also included adjacent to the first end 122 and second end 124 of the segments 110A, 110B are two or more slots 120 that each receive a cable guide element. In one embodiment the cable guide element is a seaming pin 150 that holds the adjacent segments together. As shown in FIG. 3C, the pin 150 has a head 152 sized to prevent the pin 150 from being pulled through the slot 120 and a tab 154 that fits into the slots 120 of the adjacent segments. The distal end of the tab 154 includes a hole 156 that forms a passage through which a control cable can be passed. In some embodiments, two slots 120 are spaced at a 180 degree interval around the circumference of each segment 110. In other embodiments, three slots 120 are spaced at 120 degree intervals around the circumference of each segment 110. In further embodiments, four slots 120 are spaced at 90 degree intervals around the circumference of each segment 110. In some embodiments, the outer extending portion of the slots 120 are a counter-bored detail for receiving the head 152 on the pin 150. In a preferred embodiment, the pins 150 are injection molded.

Figure 4:
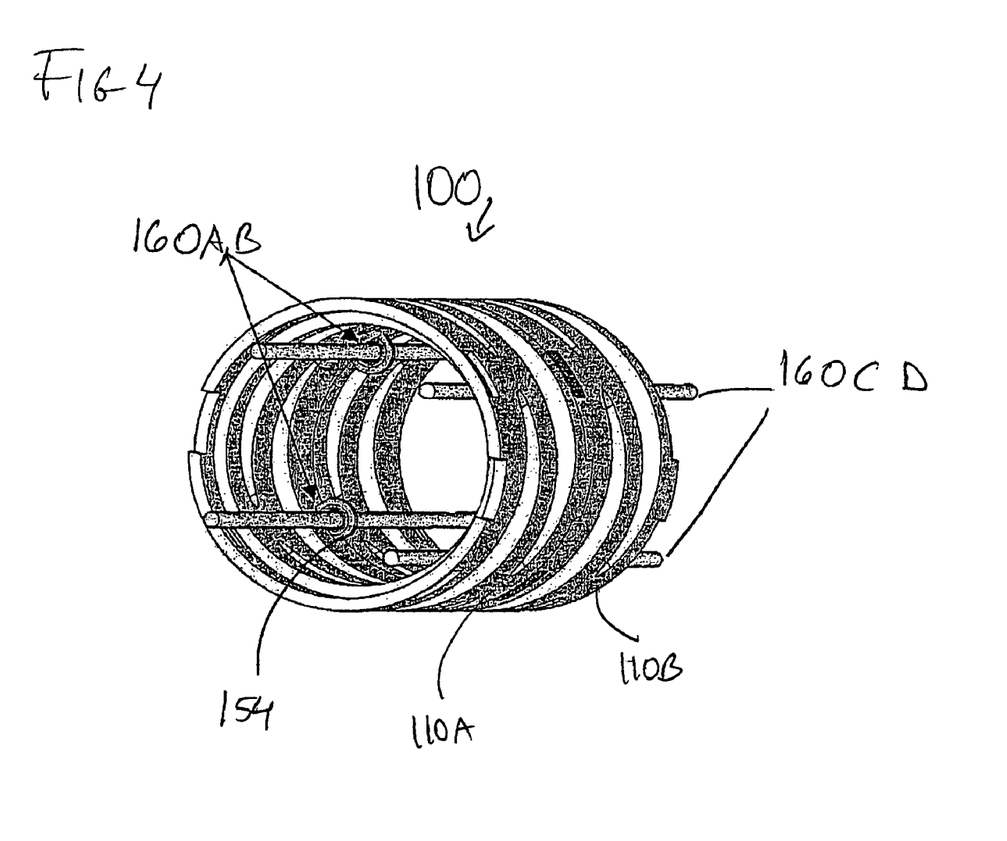
FIG. 4 is a partial perspective view of an articulation joint body comprising interconnected segments having four control cables threaded through four cable guide elements in accordance with an embodiment of the present invention.

FIG. 4 is a partial perspective view of two interconnected segments 110A, 110B, including pins 150 inserted into the slots with control cables 160A, 160B, 160C, 160D threaded through the holes 156 in the tabs 154 to couple the adjacent segments together. Variations in bending and torque fidelity along the length of the articulation joint can be achieved by varying the durometer rating of materials that are used to mold the different segments. Also, as mentioned above, the flexibility of the articulation joint may be varied by changing the distance between adjacent hinges in each segment and/or by varying the angles of the V-shaped slits that form the hinges.

Figure 5A:
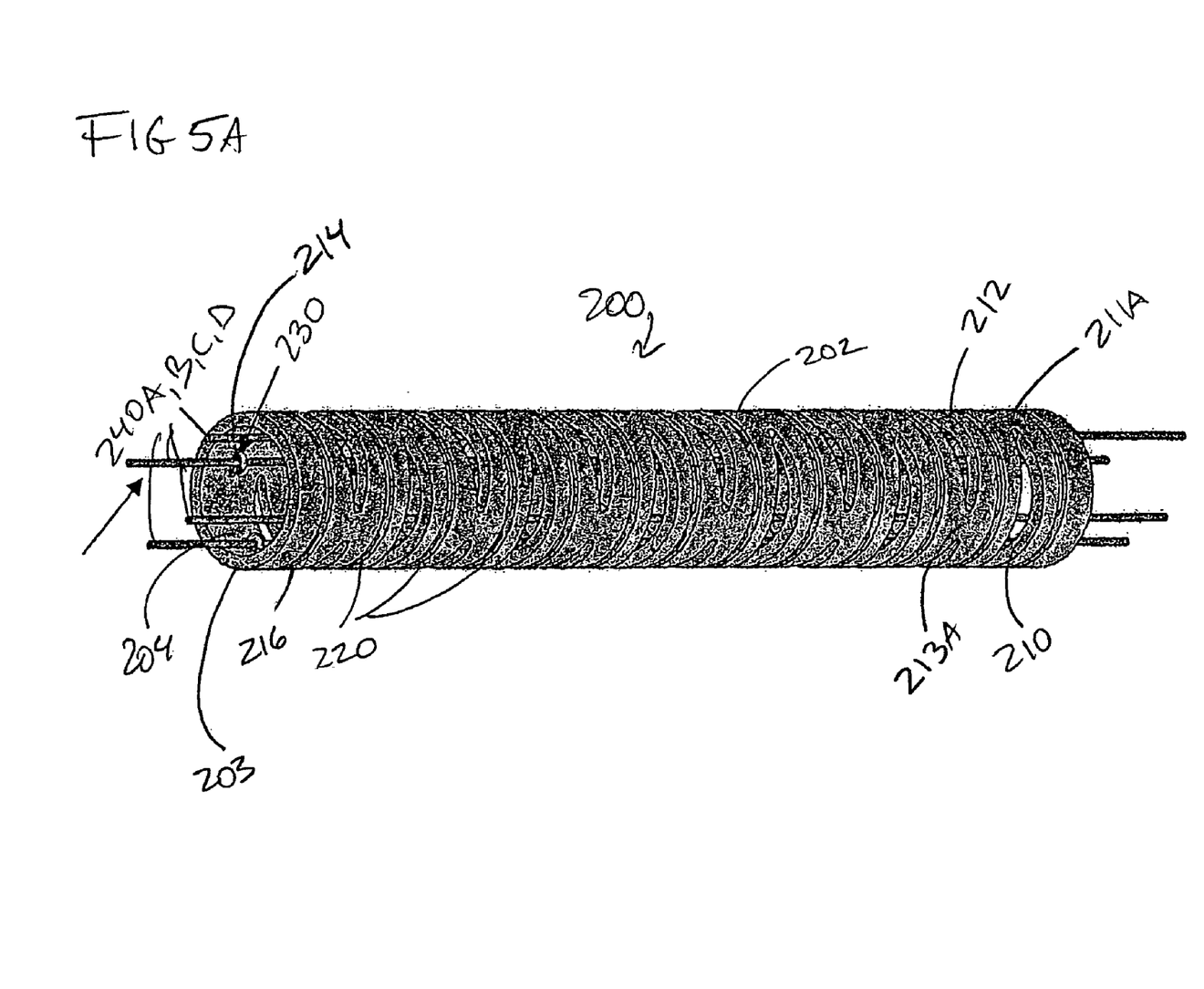
FIG. 5A is a perspective view of an embodiment of an articulation joint body comprising a unitary core having a plurality of annular rings fitted around the outer circumference of the unitary core at regular intervals, in accordance with an embodiment of the present invention.

FIG. 5A illustrates an articulation joint body 200 formed in accordance with another embodiment of the present invention. The articulation joint body 200 comprises an elongated unitary core 202 comprising a cylinder with an outer wall 203 and a central lumen 204. The outer wall 203 of the unitary core 202 comprises a series of hinges 210, 212 along its length that are oriented perpendicular to the longitudinal axis of the elongated unitary core 202. As shown in FIG. 5A, each hinge 210, 212 comprises a pair of opposing V-shaped slits in the outer wall 203 that are separated by a pair of opposing flex points 211A, 211B (hidden in FIG. 5A) and 213A, 213B (hidden in FIG. 5A) in the outer wall 203. In the embodiment of the articulation joint body 200 shown in FIG. 5A, the hinges 210 and 212 are arranged in an alternating 90 degree pattern, although other arrangements would also be known to one of skill in the art. The outer wall 203 also includes a plurality of circumferential grooves 216 located on the outside of the outer wall 203 at intervals spaced along the length of the unitary core 202. Each circumferential groove 216 is sized to receive an annular ring 220, best shown in FIG. 5B. Each circumferential groove 216 further includes one or more slots 214, best shown in FIG. 5C. Each slot 214 is adapted to receive an inwardly extending cable guide loop 230 that fits through the slot 214 such that a control cable can fit in the space between the inner wall of the shaft and the enclosed portion of the loop 230. In one embodiment, one circumferential groove 216 is disposed between hinges 210 and 212 to form an alternating pattern, as shown in FIG. 5A.

The elongated unitary core 202 may be formed by injection molding using a suitable biocompatible polymeric material, such as polyurethane, polyethylene, polypropylene or other biocompatible polymers.

Figure 5B:
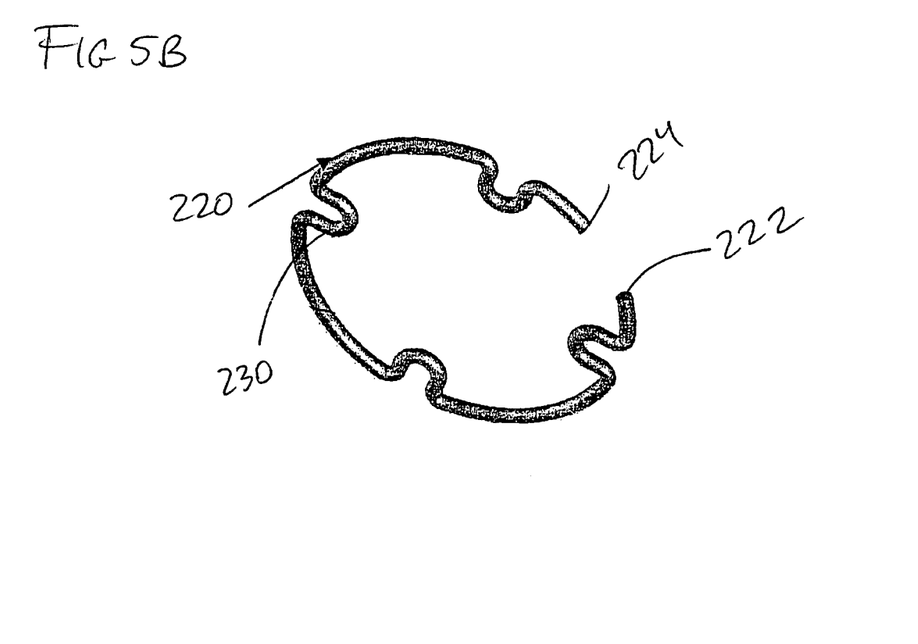
FIG. 5B is a detailed view of the embodiment of the annular ring shown in FIG. 5A.

FIG. 5B illustrates an embodiment of the annular ring 220 that comprises an outer circumference with a first end 222 and a second end 224 having a space therebetween that allows the annular ring 220 to be snap-fitted over the outer wall 203 of the unitary core 202. Positioned at equally spaced intervals around the outer circumference of the annular ring 220 are inwardly extending cable guide loops 230 that are adapted to be inserted into the corresponding slots 214 and are capable of receiving a control cable 240. One or more annular rings 220 may be disposed within the circumferential grooves 216 in the outer wall 203 of the unitary core 202, as shown in FIG. 5A.

In the embodiment shown in FIG. 5B, the annular ring 220 has four cable guide loops 230 inserted through the slots 214, through which four control cables 240A, 240B, 240C and 240D are threaded. However, a different number of cable guide loops and control cables may be provided, such as 2, 3, 4, or more than 4. The annular ring 220 may be made of a metal such as steel, brass, nitinol, etc., or molded from a biocompatible polymer.

Figure 5C:
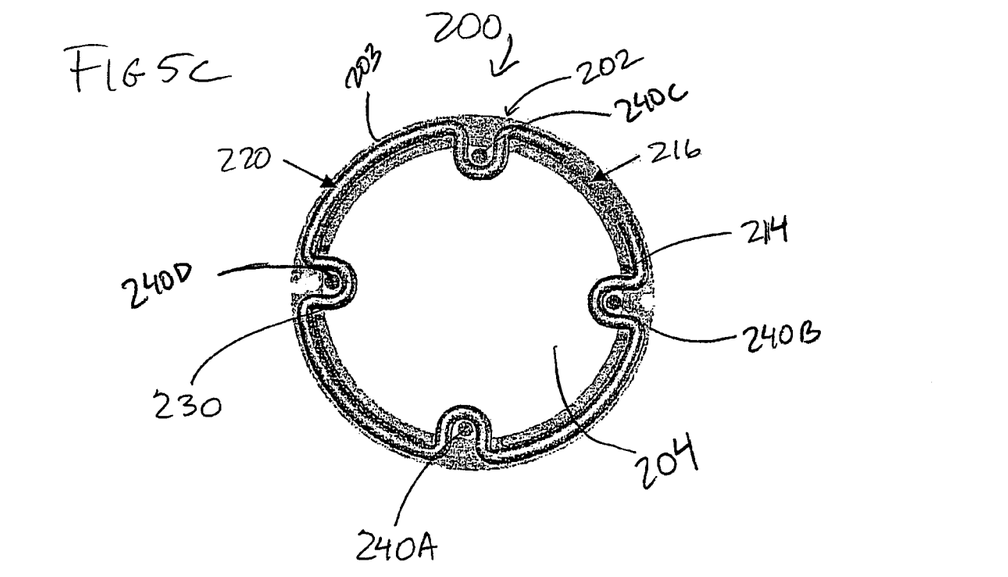
FIG. 5C is a cross-sectional view of the embodiment of the articulation joint body shown in FIG. 5A.

FIG. 5C is a cross-sectional view of the articulation joint body 200 shown in FIG. 5A, showing the annular ring 220 fitted into the circumferential groove 216 formed in the outer wall 203 of the unitary core 202. In the embodiment shown, each circumferential groove 216 includes four slots 214. As shown, the four inwardly extending cable guide loops 230 protrude towards the central lumen 204 through the slots 214, to form guides through which control cables 240A, 240B, 240C and 240D are threaded.

Figure 6:
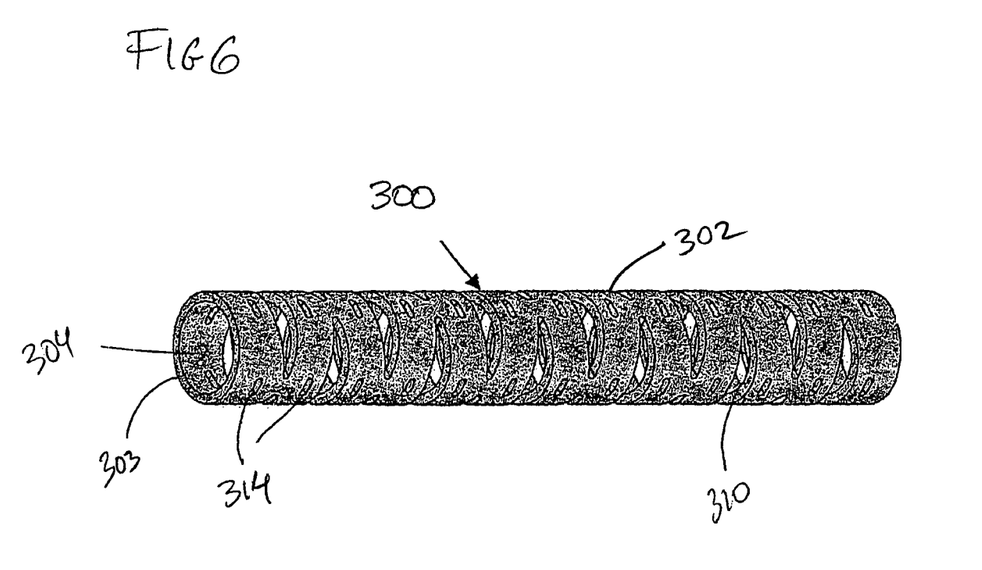
FIG. 6 is a perspective view of another embodiment of an articulation joint body comprising a unitary core having a plurality of slots, in accordance with an embodiment of the present invention.

FIG. 6 shows another embodiment of an articulation joint body 300 that has a unitary core 302 formed generally as a cylinder with an outer wall 303 and a central lumen 304. The articulation joint body 300 is substantially similar to the articulation joint body 200 described above, with the difference being that the plurality of circumferential grooves 216 are omitted in the joint body 300. A series of slots 314 are arranged around the outer circumference of the body 302 that are adapted to receive one or more cable guide loops 230 extending inward on the annular ring 220, as shown and described in reference to FIGS. 5A, 5B and 5C.

Figure 7:
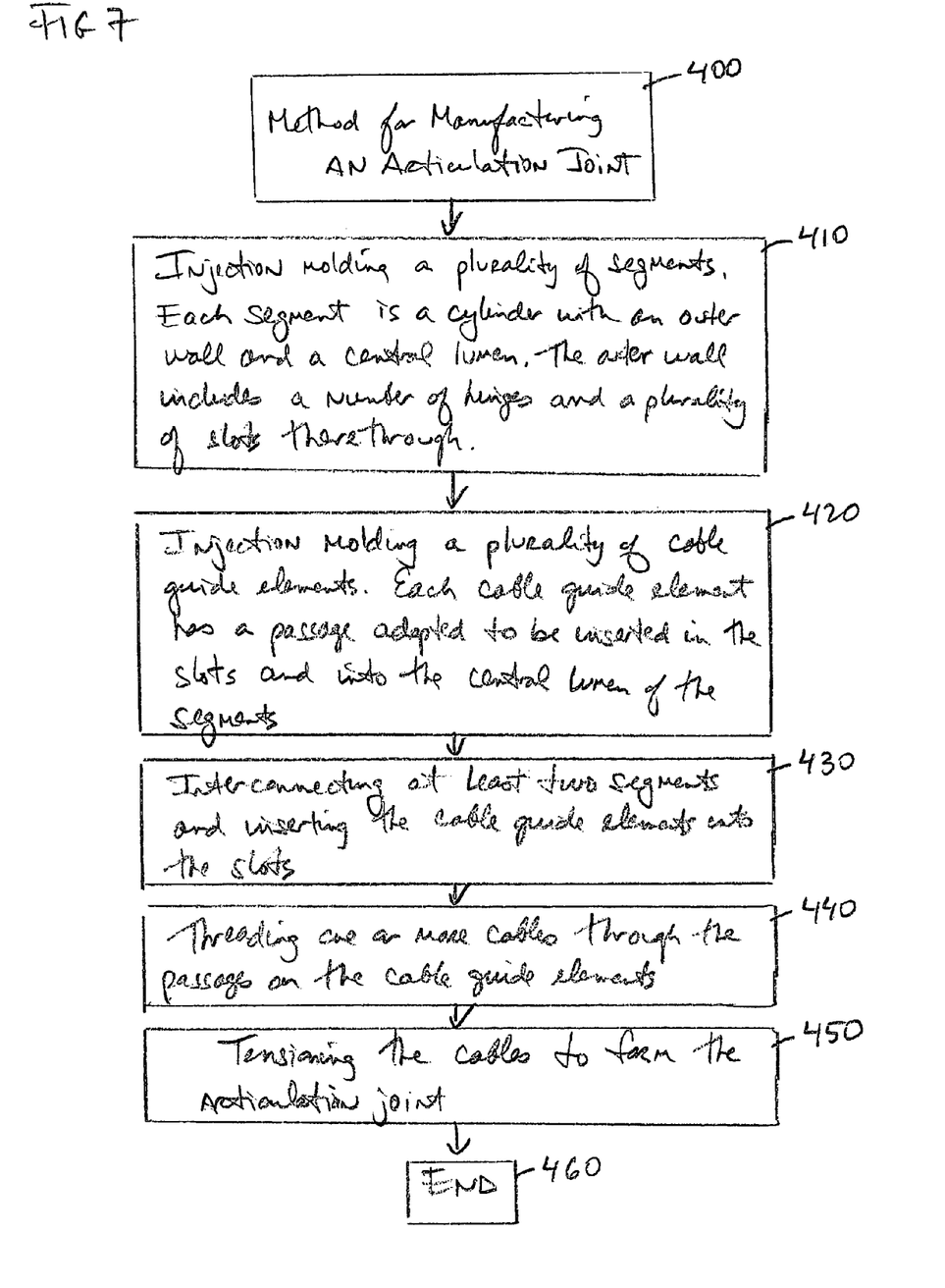
FIG. 7 is a flow diagram illustrating a method of manufacturing an articulation joint body having a plurality of interconnected segments in accordance with an embodiment of the present invention.

In another aspect, the present invention includes a method for manufacturing an articulation joint for use in a medical device, such as a low cost endoscope. FIG. 7 is a flow chart of a process for manufacturing a segmented articulation joint. The process begins at 400 and comprises injection molding a plurality of segments comprising corresponding interfacing tangs and notches at 410. The segments may be injection molded using a suitable biocompatible polymeric material, such as, for example, polyurethane, polyethylene, polypropylene or other biocompatible polymers. Each segment comprises a generally cylindrical body with an outer wall and a central lumen. The outer wall of each segment includes a number of hinge elements, such as V-shaped slits. The V-shaped slits may be molded into the segments or cut with a laser, waterjet or other material removal mechanism. In some embodiments, the outer walls of the segments further include a series of slots adapted to receive a cable guide element. The process further includes injection molding a plurality of cable guide elements at 420. In one embodiment, the cable guide elements include a retaining head connected to a passage sized to be received in the slots in the outer wall of the segments. The cable guide elements may be injection molded from a metal such as steel, brass, etc. or from a biocompatible polymer. At 430 a plurality of segments are interconnected by aligning the corresponding tangs and notches on each segment. Any number of segments may be connected together in order to provide various degrees of articulation. The passages of the plurality of guide elements are inserted into the slots on the interconnected segments. Once the cable guide elements are in place, cables are threaded through the corresponding cable passages at 440. The cables are then tensioned to form the articulation joint at 450. The cables are preferably made of a non-stretching material such as a stainless steel or a highly oriented polyethylene-terephthalate (PET) thread string. The method ends at 460.

Figure 8:
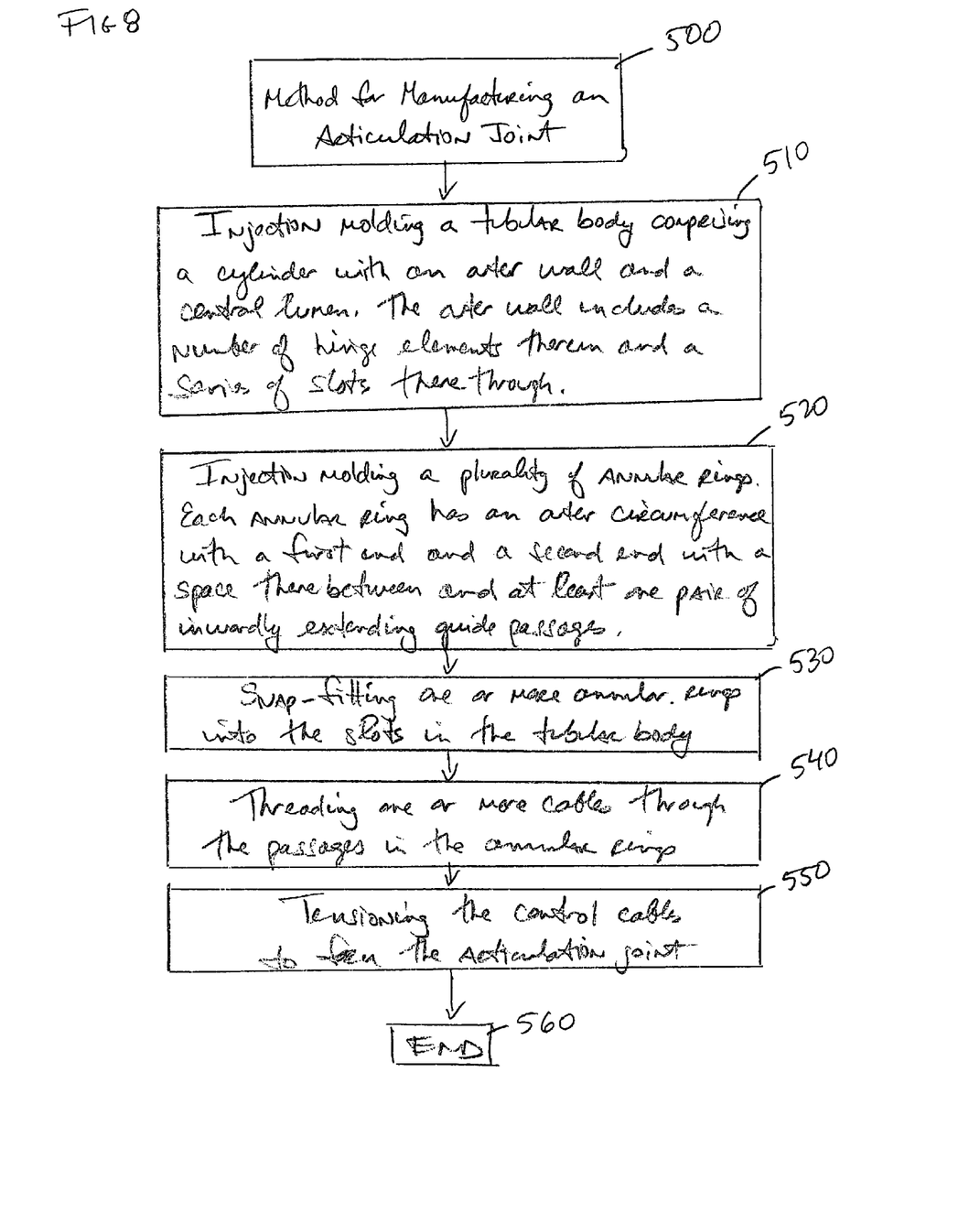
FIG. 8 is a flow diagram illustrating a method of manufacturing an articulation joint body having a unitary core in accordance with another embodiment of the present invention.

In another embodiment, the present invention provides a method for manufacturing an articulation joint comprising a unitary core as shown in FIG. 8. The process starts at 500 and comprises injection molding a tubular body comprising a cylinder with an outer wall and a central lumen. The outer wall comprises a plurality of hinge elements such as V-shaped slits. In one embodiment, the outer wall includes a series of slots arranged around the circumference of the outer wall that are each adapted to receive a guide passage on an annular ring. In another embodiment, the outer wall further includes a series of circumferential grooves that are disposed over the slots. At 520 the process further includes injection molding, stamping, or otherwise forming a plurality of annular rings that each comprise an outer circumference with a first end and a second end having a space therebetween that allows the ring to be snap-fitted over the outer wall and received in one of the circumferential grooves. Each annular ring also includes two or more oppositely formed, inwardly extending guide passages that are adapted to be received in the slots in the outer wall. The annular rings may be formed from a metal such as steel, brass, etc. or from a biocompatible polymer. At 530 the plurality of annular rings are snap-fitted over the tubular body such that the guide passages extend through the slots towards the central lumen. Once the annular rings are in place, one or more cables are threaded through the guide passages at 540. The threaded cables are then tensioned at 550 to form an articulation joint. The process ends at 560.

While the preferred embodiment of the invention has been illustrated and described, it will be appreciated that various changes can be made therein without departing from the scope of the invention. It is therefore intended that the scope of the invention be determined from the following claims and equivalents thereof.

The embodiments of the invention in which an exclusive property or privilege is claimed are defined as follows:

1. An articulation joint for use in a medical device, the articulation joint comprising a tubular body comprising:
   a plurality of interconnected adjacent segments, wherein each segment comprises a generally cylindrical tube with a first end, a second end, an outer wall, and a central lumen, wherein the first end of a first segment of the plurality of segments includes a tang that interlocks with a notch on the second end of an adjacent segment to form a non-articulating interface substantially preventing all rotational movement between the first end of the first segment and the second end of the adjacent segment, and wherein the outer wall of each segment includes at least one hinge element therein and at least one slot therethrough;
   at least one cable guide element comprising a passage, wherein the at least one cable guide element is configured to at least partially extend through the at least one slot and to at least partially reside within the at least one slot; and one or more control cables threaded through the at least one cable guide element comprising the passage.

2. The articulation joint of claim 1, wherein the passage of the at least one cable guide element extends through the at least one slot and into the central lumen of the segment.

3. The articulation joint of claim 1, wherein the at least one cable guide element comprises a retaining head connected to the passage, wherein the retaining head prevents the cable guide element from passing through the at least one slot.

4. The articulation joint of claim 1, wherein the at least one cable guide element comprises an annular ring comprising an outer circumference with a first end and a second end having a space therebetween, wherein the space is sized to allow the annular ring to be fitted around the circumference of the tubular body at spaced intervals.

5. The articulation joint of claim 4, wherein the annular ring comprises at least one pair of inwardly extending cable guide passages adapted to be inserted through the slots and into the central lumen.

6. The articulation joint of claim 1, wherein each segment includes at least two hinge elements therein and a series of slots therethrough.

7. The articulation joint of claim 6, wherein each segment includes at least two V-shaped slits oriented generally transverse to a longitudinal axis of the generally cylindrical tube to provide flexibility along a first axis that is generally transverse to the longitudinal axis.

8. The articulation joint of claim 7, wherein each segment further includes at least two V-shaped slits oriented to provide flexibility along a second axis that is generally transverse to the longitudinal axis, and wherein the first axis is generally orthogonal to the second axis.

9. The articulation joint of claim 8, wherein the V-shaped slits each have a closing angle between each side of the V-shaped slit of about 30 degrees.

10. The articulation joint of claim 1, wherein the articulation joint comprises at least six interconnected adjacent segments.

11. The articulation joint of claim 1, wherein the plurality of segments are molded.

12. The articulation joint of claim 11, wherein the plurality of segments are molded from a biocompatible polymeric material.

13. The articulation joint of claim 1, wherein the articulation joint comprises at least two segments molded from polymeric materials having durometer values that differ from one another.

14. The articulation joint of claim 1, wherein the one or more control cables threaded through the at least one cable guide element are tensioned to couple the plurality of adjacent segments together to form the tubular body.

15. The articulation joint of claim 1, wherein the at least one hinge element includes at least two V-shaped slits separated by a flex point.

16. The articulation joint of claim 1, wherein the generally cylindrical tube includes a cylinder.

17. The articulation joint of claim 1, wherein the at least one slot includes a counterbore configured to receive a head of the at least one cable guide element.

18. The articulation joint of claim 1, wherein a first segment of the plurality of interconnected adjacent segments includes a first slot, a second segment of the plurality of interconnected adjacent segments includes a second slot, and the first slot and second slot are aligned to receive the at least one cable guide.

19. An articulation joint segment for use in a medical device, the articulation joint segment comprising:

a tubular body having a proximal end, a distal end, and an outer wall;

a lumen extending from the proximal end of the tubular body to the distal end of the tubular body;

a hinge section of the outer wall having a hinge configured to permit lateral movement of the articulation joint segment;

a non-hinged section of the outer wall having an end including a tang configured to interlock with a notch on a corresponding end of an adjacent articulation joint segment to form a non-articulating interface substantially preventing all rotational movement between the end and the corresponding end, wherein the non-hinged section has a slot at least partially extending through the outer wall, and wherein the slot is configured to receive a cable guide having a passage extending therethrough; and a control member moveably located within the passage of the cable guide to control lateral movement of the articulation joint segment.

20. The articulation joint segment of claim 19, further including two lateral slots, wherein a first slot is proximally located and a second slot is distally located.

21. The articulation joint segment of claim 20, wherein the first slot is configured to align with a second slot of a second articulation joint segment to permit the cable guide to at least partially reside within the first slot and the second slot to substantially hold the articulation joint segment and the second articulation joint segment together.

22. The articulation joint segment of claim 19, wherein the slot includes a counterbore configured to receive a head of the cable guide.

23. The articulation joint segment of claim 19, wherein the hinge and the slot are located at different positions along a common longitudinal axis of the tubular body.

24. The articulation joint segment of claim 19, wherein the control member resides generally within the lumen of the tubular body.

25. The articulation joint segment of claim 19, wherein the hinge section includes a generally V-shaped slit formed in the outer wall.

26. The articulation joint segment of claim 25, wherein the generally V-shaped slit has a closing angle of about 30 degrees between each side of the generally V-shaped slit.

27. The articulation joint segment of claim 19, wherein the hinge is formed from a molded plastic material configured to flex to cause lateral movement of the articulation joint segment.

28. An articulation joint for use in a medical device, comprising:

a single elongate polymeric structure formed from a single mold and having a proximal end region, a distal end region, and an outer wall, the outer wall having an end including a tang configured to interlock with a notch on a corresponding end of an adjacent articulation joint to form a non-articulating interface substantially preventing all rotational movement between the end and the corresponding end;

a lumen that extends within the elongate polymeric structure from a generally distal location to a generally proximal location;

a plurality of hinge elements located between the proximal end region and the distal end region and formed within the elongate polymeric structure;

a plurality of slots located within the proximal end region and the distal end region, formed within the elongate polymeric structure, and configured to receive a plurality of cable guides; and at least one control member located generally within the lumen and operatively connected to the plurality of cable guides.

29. The articulation joint of claim 28, wherein the elongate polymeric structure includes a plurality of V-shaped slits circumferentially arranged about the outer wall.

30. The articulation joint of claim 28, wherein the at least one control member includes two control cables.

* * * * *